US011904267B2

(12) United States Patent
Vandyke et al.

(10) Patent No.: US 11,904,267 B2
(45) Date of Patent: *Feb. 20, 2024

(54) APPARATUS AND METHOD FOR IRRADIATING AIR IN AN AIR CIRCULATION SYSTEM OF A VEHICLE (71) Applicant: THE BOEING COMPANY, Chicago, IL (US)

(72) Inventors: Bryce A. Vandyke, Everett, WA (US); Kevin S. Callahan, Shoreline, WA (US); Stephen M. Trent, Seattle, WA (US)

(73) Assignee: The Boeing Company, Arlington, VA (US)

(*) Notice: Subject to any disclaimer, the term of this patent is extended or adjusted under 35 U.S.C. 154(b) by 359 days.

This patent is subject to a terminal disclaimer.

(21) Appl. No.: 17/192,366

(22) Filed: Mar. 4, 2021

(65) Prior Publication Data

US 2021/0394103 A1 Dec. 23, 2021

Related U.S. Application Data (60) Provisional application No. 63/041,709, filed on Jun. 19, 2020.

(51) Int. Cl.
*B01D 46/00* (2022.01)
*A61L 9/014* (2006.01)
(Continued)

(52) U.S. Cl.
CPC .......... *B01D 46/0028* (2013.01); *A61L 9/014* (2013.01); *A61L 9/20* (2013.01);
(Continued)

(58) Field of Classification Search
CPC ............ B01D 46/0028; B01D 46/0004; B01D 46/4245; B01D 46/442; B01D 46/444; B01D 46/521; A61L 9/20; A61L 9/014
See application file for complete search history.

(56) References Cited

U.S. PATENT DOCUMENTS 5,997,619 A * 12/1999 Knuth ................ B01D 46/0038
55/385.2
6,783,578 B2  8/2004 Tillman, Jr.
(Continued)

FOREIGN PATENT DOCUMENTS

CN  103446879 A   12/2013
JP  H10249128 A    9/1998
(Continued)

OTHER PUBLICATIONS

European Extended Search Report and Written Opinion issued in connection with European Patent Application No. 21171098.3 dated Oct. 5, 2021, pp. 12.

*Primary Examiner* — Robert Clemente
(74) *Attorney, Agent, or Firm* — Armstrong Teasdale LLP (57) ABSTRACT

An apparatus for irradiating air flow in a vehicle includes a filter unit configured to couple to a recirculating-air conduit connected to a manifold of an air circulation system, the filter unit having an inlet end, and a filter disposed in the inlet end of the filter unit, including an outer wall of filter media having a shape that defines an interior volume of the filter. The apparatus further includes an ultraviolet light disposed on an end plate, configured to be mounted with the ultraviolet light positioned in the interior volume of the filter and the end plate against an open end of the filter. The ultraviolet light is configured to emit ultraviolet radiation substantially at between 222 nm and 265 nm for irradiating air flow through the filter into the air circulation system.

19 Claims, 5 Drawing Sheets (51) Int. Cl.
    *A61L 9/20*     (2006.01)
    *B01D 39/20*     (2006.01)
    *B01D 46/24*     (2006.01)
    *B01D 46/42*     (2006.01)
    *B01D 46/44*     (2006.01)
    *B01D 46/52*     (2006.01)
    *B64D 13/06*     (2006.01)

(52) U.S. Cl.
    CPC ..... *B01D 39/2055* (2013.01); *B01D 46/0004* (2013.01); *B01D 46/0005* (2013.01); *B01D 46/2414* (2013.01); *B01D 46/4245* (2013.01); *B01D 46/442* (2013.01); *B01D 46/444* (2013.01); *B01D 46/521* (2013.01); *B64D 13/06* (2013.01); *A61L 2209/12* (2013.01); *A61L 2209/14* (2013.01); *A61L 2209/15* (2013.01); *A61L 2209/16* (2013.01); *A61L 2209/22* (2013.01); *B01D 2265/04* (2013.01); *B01D 2279/40* (2013.01); *B01D 2279/65* (2013.01); *B64D 2013/0651* (2013.01); *B64D 2013/0688* (2013.01)

(56) References Cited

U.S. PATENT DOCUMENTS

| | | | |
|---|---|---|---|
| 2004/0112221 A1* | 6/2004 | Tillman, Jr. | B01D 46/2411 |
| | | | 96/226 |
| 2018/0250430 A1 | 9/2018 | Machovian et al. | |
| 2019/0009912 A1 | 1/2019 | Matsui | |
| 2021/0393841 A1* | 12/2021 | Vandyke | B64D 13/06 |

FOREIGN PATENT DOCUMENTS

| | | |
|---|---|---|
| JP | 2017074943 A | 4/2017 |
| KR | 20120047175 A | 5/2012 |
| WO | 2017101618 A1 | 6/2017 |
| WO | 2019195217 A1 | 10/2019 |

* cited by examiner

APPARATUS AND METHOD FOR IRRADIATING AIR IN AN AIR CIRCULATION SYSTEM OF A VEHICLE

CROSS-REFERENCE TO RELATED APPLICATIONS

The present application claims priority to U.S. Provisional Patent Application No. 63/041,709, filed Jun. 19, 2020, the entire contents of which are incorporated by reference herein.

FIELD

The present disclosure relates to irradiation treatment of air within an air circulation system of a vehicle, and more particularly to air purification for use with cooling and environmental control systems onboard an aircraft.

BACKGROUND

This section provides background information related to the present disclosure which is not necessarily prior art. Cabin air systems in example vehicles and aircraft are designed to provide a comfortable cabin environment. In some example aircraft, the aircraft cabin is pressurized to enable passengers and crew to breathe normally. Air enters a passenger area from overhead distribution outlets that run a length of the aircraft cabin and generate airflow within the cabin. Air supplied to the cabin contains a mixture of recirculated air from within the cabin and air from outside the aircraft. Air is exhausted through air returns located along the length of the cabin, such that air is supplied to and exhausted from the passenger area on a continuous basis.

Other vehicles, such as trains and buses, have air circulation systems that circulate air for purposes of passenger comfort. In many vehicles, there is a centralized air unit that may circulate both external air introduced into the vehicle as well as air re-circulated inside the vehicle, where contaminants and airborne particulates may be present in the air. Airborne particulates include a complex mixture of organic and inorganic substances, including bacteria, germs, a variety of airborne viruses, and other substances that are small enough to become suspended in the air, where exposure of passengers to airborne particulates poses risks of infection and contagion.

Those skilled in the art will readily appreciate that all of the above-mentioned issues may represent significant considerations with respect to the overall operations of an airline or other vehicle operator. Thus, there exists a continuing need for an improved, cost-effective approach for circulating air within a vehicle.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

SUMMARY

This section provides a general summary of the disclosure, and is not a comprehensive disclosure of its full scope or all of its features.

According to various aspects, an apparatus for irradiating air within an air circulation system of a vehicle includes a filter unit to couple to a recirculating air conduit that is coupled to an air circulation system. A filter is disposed in an inlet end of the filter unit, and has a shape defining an interior volume of the filter. The apparatus further includes an ultraviolet light disposed on an end plate, for mounting with the ultraviolet light positioned in the interior volume of the filter and the end plate against an open end of the filter. The ultraviolet light can emit ultraviolet radiation between 222 nm and 265 nm for irradiating air flow through the filter.

According to another aspect, a method for irradiating air in an air circulation system of a vehicle includes coupling a filter unit to a recirculating air conduit that is connected to an air circulation system. The method includes positioning a filter within an inlet end of the filter unit, the filter having a shape that defines an interior volume of the filter. The method further includes mounting an ultraviolet light disposed on an end plate with the ultraviolet light positioned in the interior volume of the filter and the end plate positioned against an open end of the filter. The method also includes supplying power to an electrical connector of the ultraviolet light, via an electrical power connection disposed on the end plate, to cause the ultraviolet light to emit ultraviolet radiation substantially at between 222 nm and 265 nm for irradiating air flow through the filter.

Further areas of applicability will become apparent from the description herein. The description and specific examples in the summary are intended for purposes of illustration only and are not intended to limit the scope of the present disclosure.

Various refinements exist of the features noted above in relation to the various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of the present disclosure without limitation to the claimed subject matter.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings. According to various aspects of the present disclosure, embodiments are described of an apparatus for irradiation treatment of air within an air circulation system of a vehicle. The features, functions, and advantages discussed in the preceding section can be achieved independently in various embodiments or may be combined in yet other embodiments. Further aspects of the present disclosure can be seen with reference to the drawings and following described embodiments.

In an example, an apparatus for irradiation treatment of air within an air circulation system of a vehicle includes a filter unit configured to couple to a recirculating-air conduit connected to a manifold of an air circulation system, the filter unit having an inlet end, and a filter disposed in the inlet end of the filter unit, including an outer High Efficiency Particulate Air (HEPA) media, and optionally an inner activated carbon filter media defining an interior volume of the filter. The apparatus further includes an ultraviolet light disposed on an end plate, configured to be mounted with the ultraviolet light positioned in the interior volume of the filter and the end plate against an open end of the filter, wherein the ultraviolet light is configured to emit ultraviolet radiation substantially at between 222 nm and 265 nm for irradiating air flow through the filter into the air circulation system.

Figure 1:
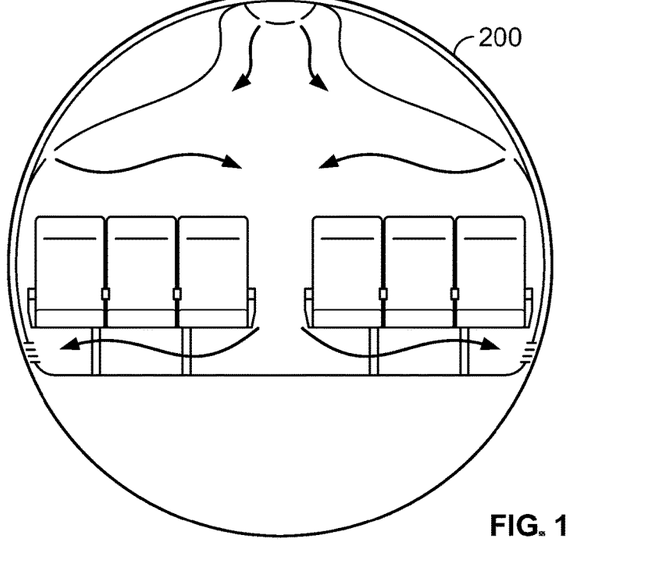
FIG. 1 is an illustration of a vehicle including an aircraft, the vehicle having a passenger air distribution system that receives air from an air circulation system, according to the present disclosure.

Referring to FIG. 1, a vehicle including an aircraft 200 has a passenger air distribution system that receives air from an air circulation system. The air distribution system supplies air that enters a passenger area from overhead distribution outlets that run a length of the aircraft cabin and generate airflow in the cabin. Air supplied to the cabin contains a mixture of recirculated air from in the cabin and air from outside the aircraft. Air is drawn through air returns located near the floor along the length of the cabin, such that air is supplied to and removed from the cabin passenger area on a continuous basis.

Figure 2:
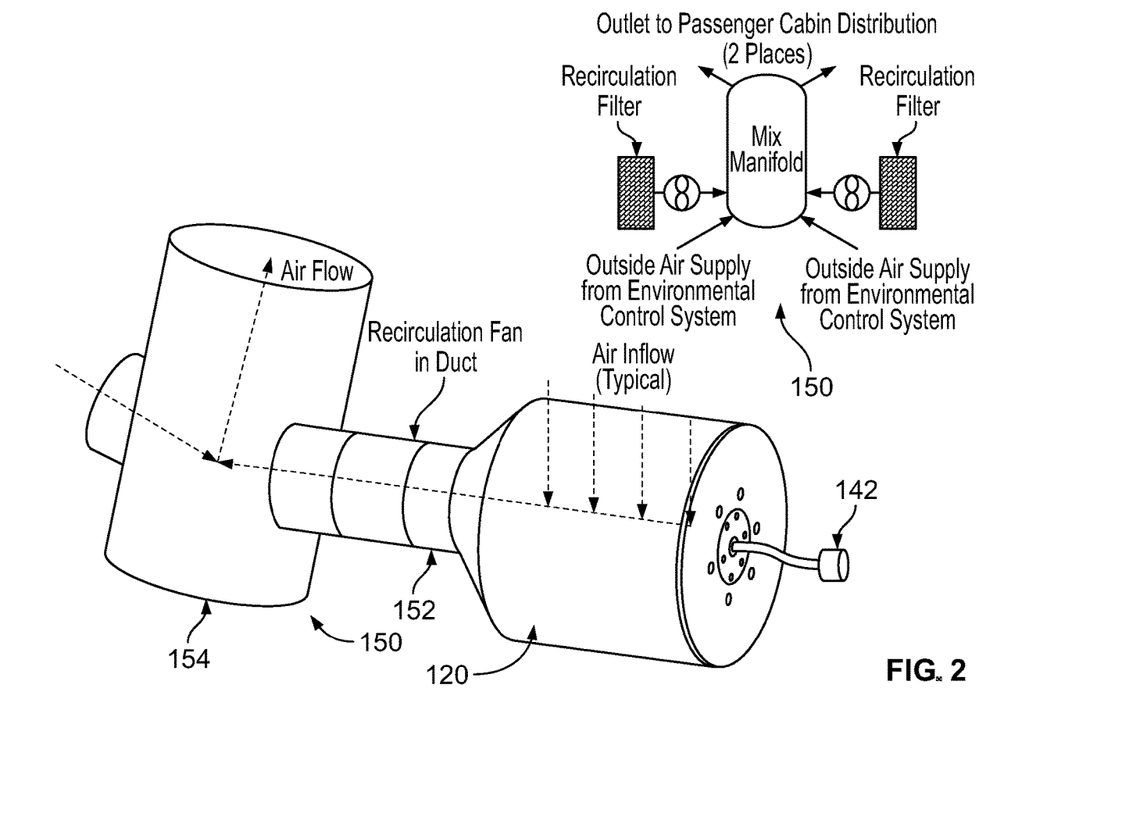
FIG. 2 is an illustration of an air circulatory system of a vehicle including an embodiment of an apparatus for irradiating air flow to the air circulation system, according to the present disclosure.

FIG. 2 is an illustration of an air circulation system 150 of a vehicle—such as the aircraft 200 shown in FIG. 1—including an embodiment of an apparatus for irradiating air flow to the air circulation system 150. The air circulation system 150 includes a recirculating air conduit 152 (in which a recirculating fan may be disposed) that is connected to a mix manifold 154 of the air circulation system 150, where the mix manifold 154 receives supply of outside air from outside the aircraft 200 from an Environmental Control System (ECS) and also receives recirculated air via filtered inputs. The mix manifold 154 also supplies two air distribution lines to supply circulated air to passengers in the cabin.

Figure 3:
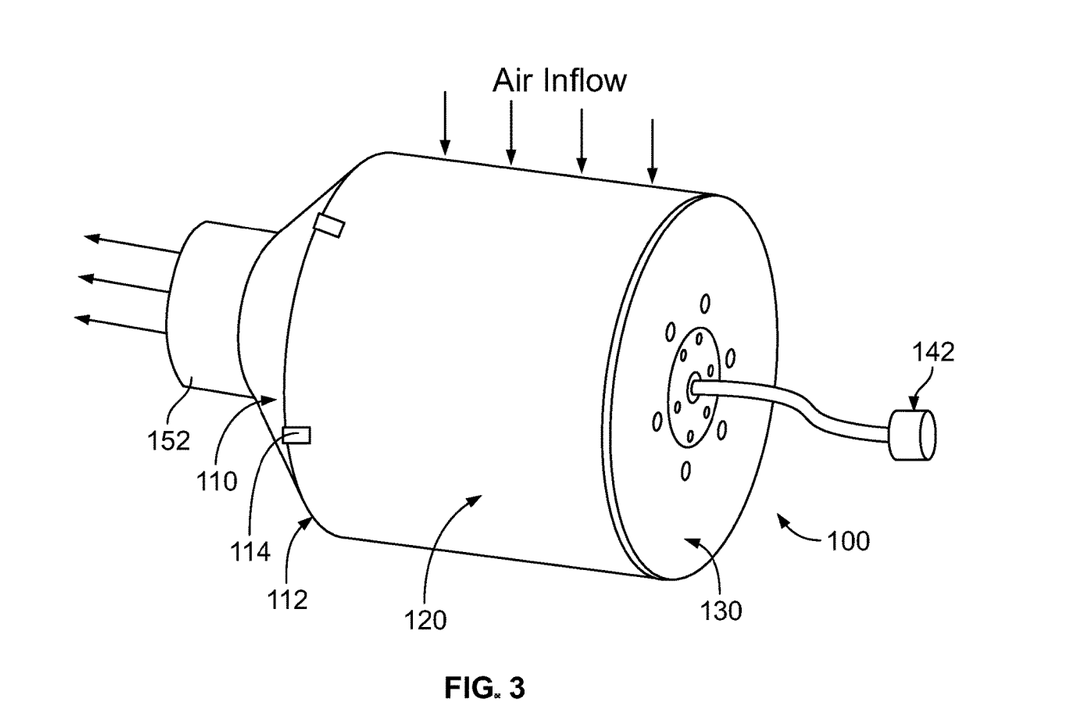
FIG. 3 is an illustration of an embodiment of an apparatus for irradiating air flow in the air circulation system for a vehicle, such as that shown in FIGS. 1 and 2, according to the present disclosure.

FIG. 3 depicts an embodiment of an apparatus 100 for irradiation treatment of air within an air circulation system 150 such as that shown in FIG. 2, for a vehicle such as aircraft 200 in FIG. 1. The apparatus 100 includes a filter unit 110 configured to couple to a recirculating air conduit 152 connected to the mix manifold 154 of the air circulation system 150, where the filter unit 110 has an inlet end 112. A filter 120 is disposed in the inlet end 112 of the filter unit 110, and has a wall of filter media having a shape that defines an interior volume 122 (see FIG. 6) of the filter 120. The apparatus 100 further comprises an ultraviolet light 140 (see FIG. 4) disposed on an end plate 130, configured to be mounted with the ultraviolet light 140 positioned in the interior volume 122 of the filter 120 and the end plate 130 against an open end of the filter 120, wherein the ultraviolet light 140 is configured to emit ultraviolet radiation substantially at between 222 nm and 265 nm for irradiating air flow through the filter into the air circulation system 150.

In one embodiment, the apparatus 100 includes the filter unit 110 that is coupled to the recirculating air conduit 152, which is connected to the mix manifold 154 of the air circulation system 150, for supplying recirculating air to the mix manifold 154. The filter 120 is disposed at the inlet end 112 of the filter unit 110, where the filter 120 may have a circular, rectangular, or triangular shape and an outer media wall through which air is drawn, where the filter shape defines the interior volume 122 through which air passes through the media of the filter 120 to the interior volume 122. The filter 120 is disposed on and configured to couple to the filter unit 110 via tabs 114, for example.

Figure 4:
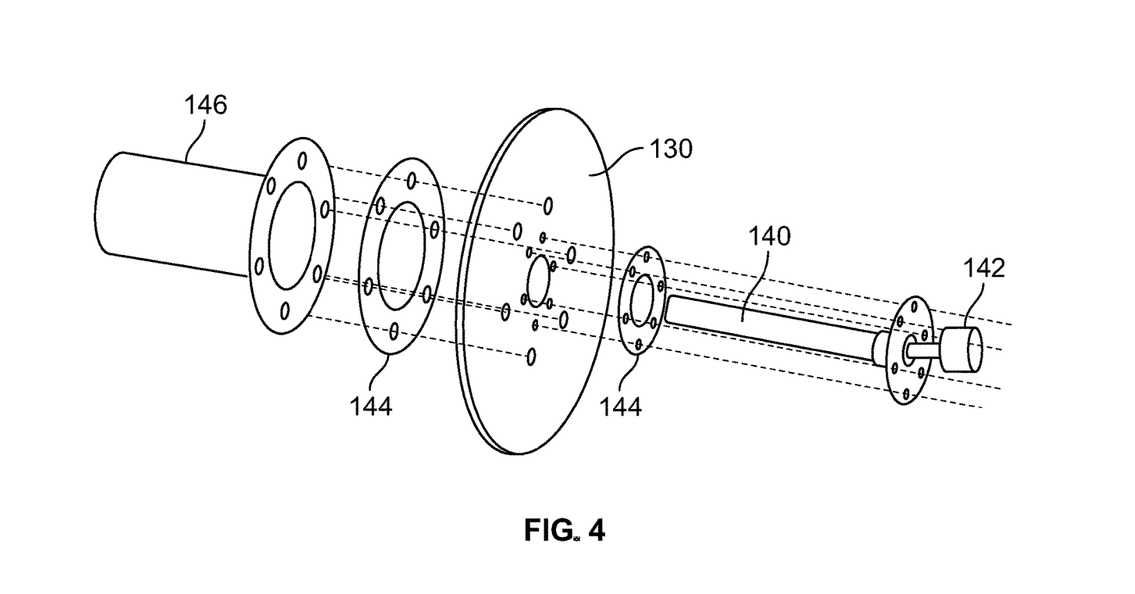
FIG. 4 is an exploded view of an embodiment of an ultraviolet light assembly of the apparatus in FIG. 3, according to the present disclosure.

In one embodiment, the apparatus 100 includes an emitter of ultraviolet light 140 and an end plate 130, as illustrated in the exploded assembly view illustrated in FIG. 4. The emitter of ultraviolet light 140 may comprise an ultraviolet bulb, or a light transmissive conduit (such as a light pipe for example) that receives emitted ultraviolet light from a fiber-optic ultraviolet emitting source or an ultraviolet light emitting diode (LED), or alternatively other suitable ultraviolet light emitters. The ultraviolet light 140 (or transmissive element receiving emitted UV light) has a free end that is configured to be positioned within the interior volume 122 (see FIG. 6) of the filter 120, and an opposite end disposed proximate the end plate 130 that includes an electrical connector 142 of the ultraviolet light 140, which may be coupled to an electrical power connection for powering the ultraviolet bulb, or alternatively to an ultraviolet light emitting source. The ultraviolet light 140 may be mounted to the end plate 130 by fasteners inserted through a plurality of holes in a flange associated with the ultraviolet light 140. The assembly of the ultraviolet light 140 and the end plate 130 may further include a clear lens 146 having a mounting flange with holes, and two gaskets 144 positioned on opposing sides of the end plate 130, which are secured via fasteners for establishing a seal over the ultraviolet light 140 (positioned within the lens 146) relative to the end plate 130. A ventilation tube may optionally be installed through the end plate 130 into the volume enclosed by the clear lens 146, so that in the event of a failed ultraviolet light bulb, any ozone or gaseous effluence from the ultraviolent light bulb or emitter may be extracted to reduce to potential of ozone leaking into the air circulation system 150. In some embodiments, the ultraviolet light 140 is selected to generate or emit ultraviolet radiation at between 222 nanometer and 265 nanometer, at a predetermined power level, such that the intensity of ultraviolet radiation is sufficient to kill and/or degrade microorganisms, viruses, bacteria, germs, mold, and other contaminants in the air flowing through the interior volume 122 of the filter 120.

Figure 5:
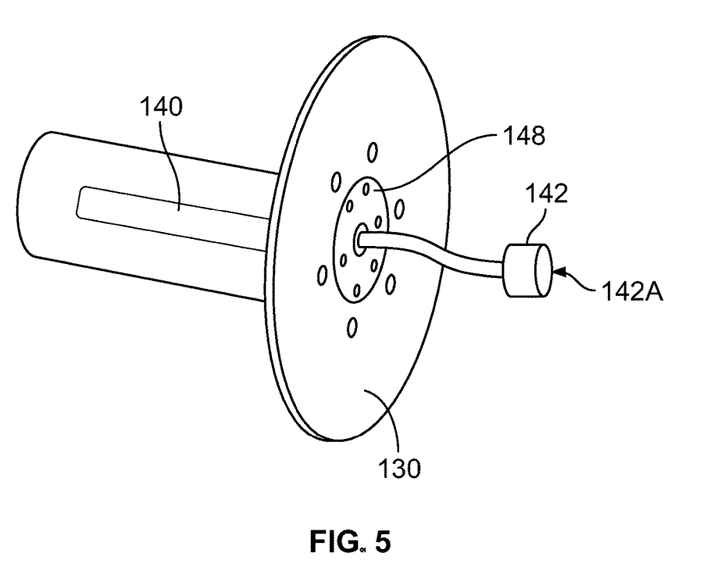
FIG. 5 is an illustration of an embodiment of an ultraviolet light and end plate in the apparatus in FIG. 3, according to the present disclosure.
Figure 6:
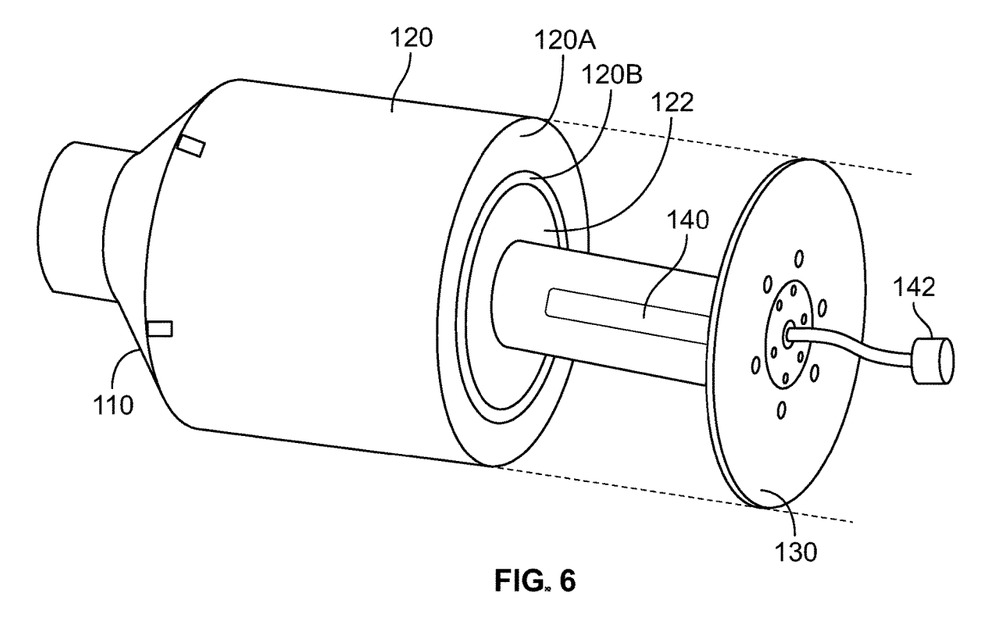
FIG. 6 is an illustration of an embodiment of an ultraviolet light and end plate relative to an open end of the filter in the apparatus in FIG. 3, according to the present disclosure.

In one embodiment, the apparatus 100 includes the ultraviolet light 140 disposed on the end plate 130 as shown in FIG. 5. The ultraviolet light 140 is configured to be mounted with the ultraviolet light 140 positioned in the interior volume 122 of the filter 120 and the end plate 130 against an open end of the filter 120, as shown in FIG. 6. The end plate 130 may be secured to the end of the filter 120 by attachment via rivets, adhesive, or bonding to the end of the filter 120. The filter 120 may have a wall of filter media forming a cylindrical shape, and includes an outer High Efficiency Particulate Air (HEPA) media 120A, and may optionally include an inner activated carbon filter media 120B defining the interior volume 122 of the filter 120, as shown in FIG. 6. In some embodiments, the outer High Efficiency Particulate Air (HEPA) media 120A includes an outer annular portion of the filter 120 forming a pleated cartridge made with a High Efficiency Particulate Air (HEPA) media. The optional inner activated carbon filter media 120B includes an inner annular portion of the filter 120 that includes activated carbon.

The ultraviolet light 140 is configured to emit ultraviolet radiation substantially at between 222 nm and 265 nm for irradiating air flow through the filter 120 into the air circulation system 150. In some embodiments, the ultraviolet light 140 is configured to emit a distribution of frequencies of ultraviolet radiation ranging substantially at between 222 nm and 265 nm, where the range is sufficient to result in generation of a minimal amount of ozone. Ultraviolet light 140 having a wavelength below 240 nm can generate ozone, while ultraviolet light having an emission frequency in the range of about 240-265 nm can potentially destroy ozone or reduce the level of ozone, where the emission of a range of ultraviolet radiation up to a frequency of 265 nm potentially reduces or limits the extent of ozone generated by emitted UV radiation at lower frequencies, such that the distribution of frequencies in the range of between 222 nm and 265 nm results in generation of a minimal amount of ozone. Additionally, the ultraviolet light 140 emits ultraviolet radiation at between 222 nm and 265 nm at a predetermined power flux or irradiation of at least 1,000 microwatts per square centimeter, such that the intensity of ultraviolet radiation is sufficient to kill and/or degrade microorganisms, viruses, bacteria, germs, mold, and other contaminants in the air flowing through the interior volume 122 of the filter 120.

Figure 7:
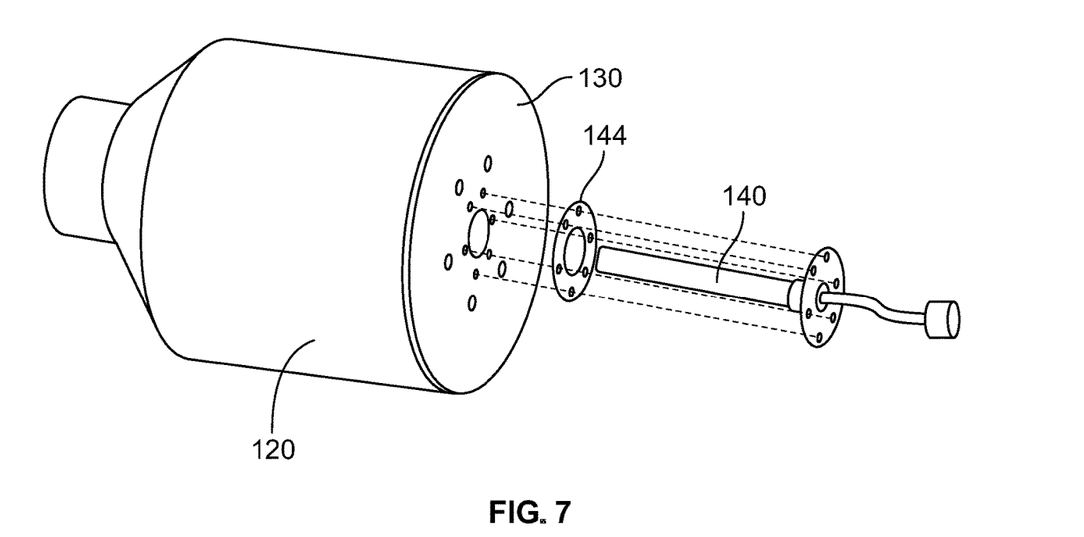
FIG. 7 is an illustration of the apparatus in FIG. 3, where the ultraviolet light shown may be removable to permit replacement.

As illustrated in FIG. 7, the ultraviolet light 140 is further configured to be removably attached to the end plate 130, to permit removal of the ultraviolet light 140 and electrical connector 142, and replacement with another ultraviolet light 140 and electrical connector 142. Because the ultraviolet light 140 may be mounted to the end plate 130 by fasteners inserted through a plurality of holes in a flange associated with the ultraviolet light 140, the ultraviolet light 140 and the flange may be separated from the end plate 130, and a replacement ultraviolet light 140 may be installed. Additionally, the apparatus 100 may be configured to provide a predetermined level of power to the ultraviolet light 140 for a predetermined period of time, such that a sufficient amount of irradiated recirculating air flows through the air circulation system 150 and is recirculated through the aircraft cabin before further flight operation of the aircraft 200. Additionally, the apparatus 100 may be configured to include a controller (not shown) that monitors an air flow sensor, mass flow sensor, or air particulate sensor disposed within the cabin of the aircraft, to determine if the amount of recirculated irradiated air flow through the aircraft cabin is indicative of a minimum level for removing airborne particulates and contaminates, and thereafter discontinuing supply of power to the ultraviolet light 140. Similarly, the controller can monitor the sensor to determine if a measurement is indicative of the presence of more than an acceptable threshold of ozone or contaminant particulates are present in the cabin air, and thereafter deactivating the ultraviolet light 140 to discontinue ultraviolet light irradiation. Additionally, the controller may monitor the sensor to determine if the amount of recirculated irradiated air flow through the aircraft cabin is indicative of an insufficient level for removing airborne particulates and contaminates, and thereafter initiate the supply of power to the ultraviolet light 140 to emit ultraviolet radiation at between 222 nm and 265 nm to irradiate the air flow through the filter 120 into the air circulation system 150.

According to another aspect, a method for irradiating air within an air circulation system of a vehicle may include coupling a filter unit to a recirculating-air conduit that is connected to a manifold of an air circulation system, the filter unit having an inlet end, and positioning a filter in the inlet end of the filter unit, the filter comprising an outer High Efficiency Particulate Air (HEPA) media, and optionally an inner activated carbon filter media defining an interior volume of the filter. The methods further include mounting an ultraviolet light disposed on an end plate, relative to the filter unit, with the ultraviolet light positioned in the interior volume of the filter and the end plate positioned against an open end of the filter, and supplying power to an electrical connector of the ultraviolet light, via an electrical power connection disposed on the end plate, to cause the ultraviolet light to emit ultraviolet radiation substantially at between 222 nm and 265 nm for irradiating air flow through the filter into the air circulation system.

Figure 8:
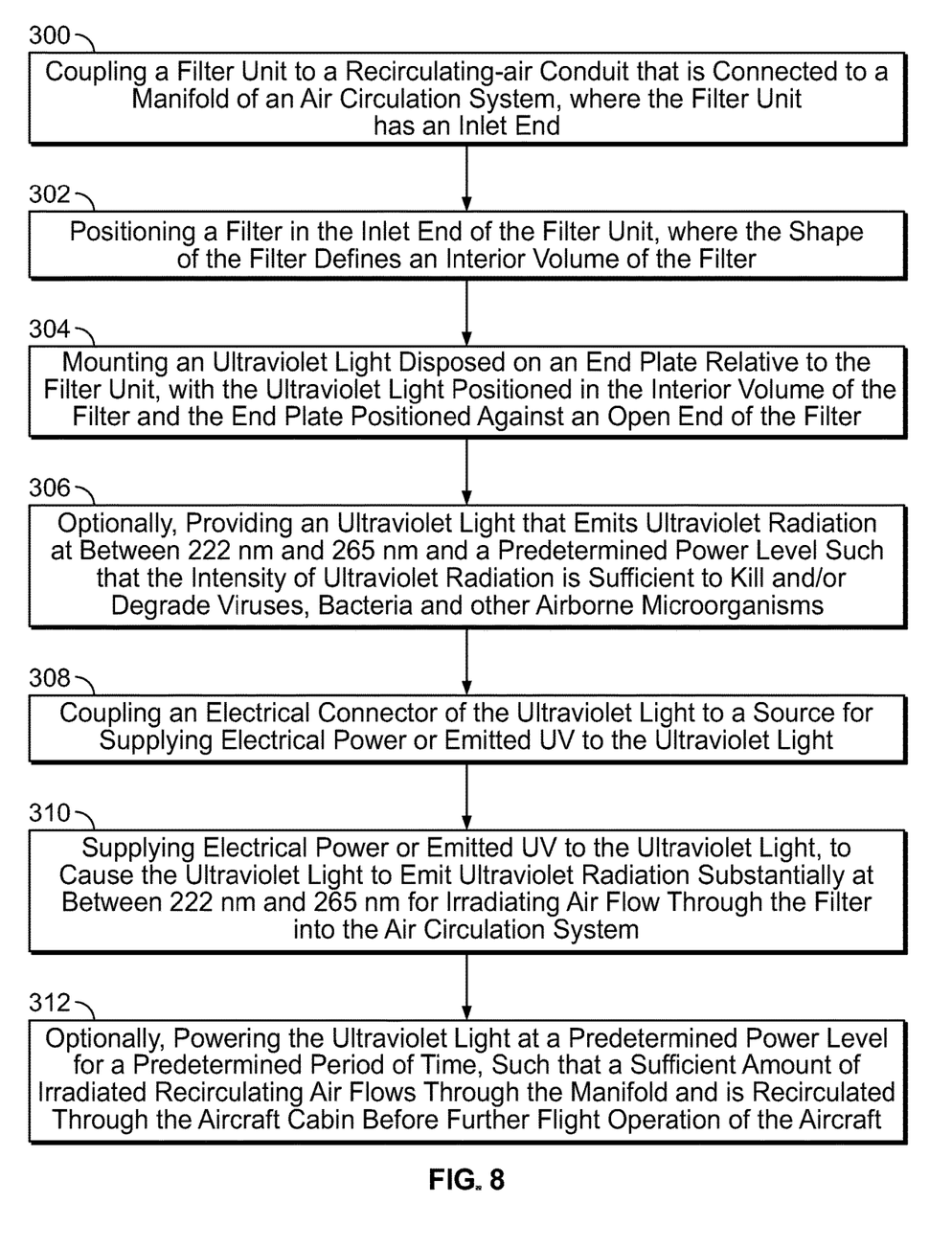
FIG. 8 is an illustration of a method for irradiating air within an air circulation system of a vehicle in accordance with the present disclosure.

As illustrated in FIG. 8, one embodiment of a method is provided for irradiating air within an air circulation system of a vehicle. The method includes at step 300 coupling a filter unit to a recirculating-air conduit that is connected to a manifold of an air circulation system, the filter unit having an inlet end. The method includes, at step 302, positioning a filter in the inlet end of the filter unit, the filter comprising an outer High Efficiency Particulate Air (HEPA) media, and optionally an inner activated carbon filter media defining an interior volume of the filter. The method further includes, at step 304, mounting an ultraviolet light disposed on an end plate, relative to the filter unit, with the ultraviolet light positioned in the interior volume of the filter and the end plate positioned against an open end of the filter. The method may optionally include the step 308 of coupling an electrical connector of the ultraviolet light to a source for supplying electrical power or a source for emitted UV light (e.g. a fiber-optic US light emitter) to the ultraviolet light. The method includes, at step 310, supplying power to an electrical connector of the ultraviolet light, via an electrical power connection disposed on the end plate, to cause the ultraviolet light to emit ultraviolet radiation substantially at between 222 nm and 265 nm for irradiating air flow through the filter into the air circulation system. The method may optionally include the step 312 of powering the ultraviolet light to emit ultraviolet radiation at a predetermined power flux or irradiation of at least 1,000 microwatts per square centimeter for a predetermined period of time, such that a sufficient amount of irradiate recirculating air flows through the air circulation system and aircraft cabin before further flight operation of the aircraft.

The example embodiments fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The invention claimed is:

1. An apparatus for irradiating air in an air circulation system of a vehicle, comprising:
   a filter unit configured to couple to a recirculating-air conduit connected to the air circulation system, the filter unit having an inlet end;
   a filter disposed at the inlet end of the filter unit, comprising a wall of filter media having a shape that defines an interior volume of the filter;
   an ultraviolet light disposed on an end plate, configured to be mounted with the ultraviolet light positioned in the interior volume of the filter and the end plate against an open end of the filter,
      wherein the ultraviolet light is configured to emit ultraviolet radiation substantially at between 222 nm and 265 nm for irradiating air flow through the filter into the air circulation system;
   a lens that encloses the ultraviolet light and is secured to the end plate to establish a sealed volume; and
   a ventilation tube extending through the end plate into the sealed volume enclosed by the lens for enabling venting and extraction of ozone or gaseous effluence released in the event of breakage or failure of the ultraviolet light, to thereby inhibit release of ozone into the air circulation system.

2. The apparatus of claim 1, wherein the ultraviolet light is configured to emit a distribution of frequencies of ultraviolet radiation ranging between 222 nm and 265 nm, where the range is sufficient to result in generation of a minimal amount of ozone.

3. The apparatus of claim 1, wherein the ultraviolet light has a free end that is configured to be positioned within the interior volume of the filter, and an opposite end disposed proximate the end plate that includes an electrical connector of the ultraviolet light that is coupled to an electrical power connection proximate to the end plate.

4. The apparatus of claim 3, wherein the ultraviolet light emits the ultraviolet radiation at between 222 nm and 265 nm at a predetermined power flux or irradiation such that an intensity of ultraviolet radiation is sufficient to kill and/or degrade microorganisms, viruses, bacteria, germs, mold, and other contaminants in the air flowing through the interior volume of the filter.

5. The apparatus of claim 1, wherein the end plate is configured to be mounted by attachment via rivets, adhesive, or bonding to the open end of the filter.

6. The apparatus of claim 3, wherein the filter comprising a wall of filter media is comprised of an outer High Efficiency Particulate Air (HEPA) media, and an inner activated carbon filter media.

7. The apparatus of claim 6, wherein the outer HEPA media comprises an outer annular portion of the filter forming a pleated cartridge made with a HEPA media, and wherein the inner activated carbon filter media comprises an inner annular portion of the filter that includes activated carbon.

8. The apparatus of claim 7, wherein the filter unit comprises a filter housing, in which the filter is disposed.

9. The apparatus of claim 8, wherein the filter housing is configured to couple to a recirculating air conduit that is connected to a manifold of the air circulation system, for supplying recirculating air to the manifold.

10. The apparatus of claim 9, wherein the manifold is a mixing manifold of an air circulating system on board an aircraft.

11. A method for irradiating air in an air circulation system of a vehicle, comprising the steps of:
   coupling a filter unit to a recirculating-air conduit that is connected to a manifold of the air circulation system, the filter unit having an inlet end;
   positioning a filter in the inlet end of the filter unit, the filter comprising an outer High Efficiency Particulate Air (HEPA) media, and an inner activated carbon filter media defining an interior volume of the filter;
   enclosing an ultraviolet light in a lens;
   securing the lens enclosing the ultraviolet light to an end plate to establish a sealed volume, relative to the filter unit, with the lens enclosing the ultraviolet light positioned in the interior volume of the filter and the end plate positioned against an open end of the filter;
   coupling a ventilation tube to the end plate, the ventilation tube extending through the end plate into the sealed volume enclosed by the lens, for enabling venting and extraction of ozone or gaseous effluence released in the event of breakage or failure of the ultraviolet light; and
   supplying power to an electrical connector of the ultraviolet light, via an electrical power connection disposed on the end plate, to cause the ultraviolet light to emit ultraviolet radiation between 222 nm and 265 nm for irradiating air flow through the filter into the air circulation system.

12. The method of claim 11, wherein the step of mounting an ultraviolet light comprises the steps of:

positioning a free end of the ultraviolet light within the interior volume of the filter; and positioning an opposite end of the ultraviolet light proximate the end plate so that the end plate is against the open end of the filter, and wherein the method further comprises the step of coupling the electrical connector of the ultraviolet light to an electrical power connection disposed on the end plate, for supplying power to the ultraviolet light.

13. The method of claim 12, wherein the method further comprises the steps of:

providing the ultraviolet light that emits ultraviolet radiation at between 222 nm and 265 nm; and powering, via the supplied power, the ultraviolet light with a predetermined power flux or irradiation such that an intensity of ultraviolet radiation is sufficient to kill and/or degrade microorganisms, viruses, bacteria, germs, mold, and other contaminants in the air flowing through the interior volume of the filter.

14. The method of claim 13, wherein the step of mounting the end plate comprises affixing the end plate to the open end of the filter by attachment via rivets, adhesive, or bonding to the open end of the filter.

15. The method of claim 14, wherein the method further comprises coupling the filter housing to a recirculating air conduit that is connected to the manifold of the air circulation system of an aircraft, for enabling supply of irradiated recirculating air to the manifold of the air circulation system for the aircraft.

16. The method of claim 15, further comprising the step of powering the ultraviolet light to power the ultraviolet light with a predetermined power level such that an intensity of ultraviolet radiation is sufficient to kill and/or degrade airborne viruses and other microorganisms in the irradiated recirculating air.

17. The method of claim 16, further comprising the step of powering the ultraviolet light to power the ultraviolet light with a predetermined power flux or irradiation for a predetermined period of time, such that a sufficient amount of irradiated recirculating air flows through the manifold and is recirculated through a cabin of the aircraft before further flight operation of the aircraft.

18. The method of claim 17, further comprising the steps of:

monitoring a sensor disposed within the cabin of the aircraft to determine if a measurement of recirculated irradiated air flow through a cabin of the aircraft is indicative of a minimum level for removing airborne particulates and contaminates; and thereafter, discontinuing supply of power to the ultraviolet light.

19. The method of claim 18, further comprising the steps of:

monitoring a sensor disposed within the cabin of the aircraft to determine if a measurement of recirculated irradiated air flow through the cabin of the aircraft is indicative of an insufficient level for removing airborne particulates and contaminates; and thereafter, supplying power to the ultraviolet light to emit ultraviolet radiation at between 222 nm and 265 nm to irradiate the air flow through the filter into the air circulation system.

* * * * *